United States Patent [19]

Claussner et al.

[11] Patent Number: 5,646,172
[45] Date of Patent: Jul. 8, 1997

[54] METHOD OF INDUCING ANTIANDROGENIC ACTIVITY USING IMIDAZOLIDINES SUBSTITUTED WITH A HETEROCYCLE

[75] Inventors: Andre Claussner, Villemomble; Francois Goubet, Paris; Jean-Georges Teutsch, Pantin, all of France

[73] Assignee: Roussel Uclaf, France

[21] Appl. No.: 524,508

[22] Filed: Sep. 7, 1995

[30] Foreign Application Priority Data

Sep. 29, 1994 [FR] France .................. 94 11649

[51] Int. Cl.$^6$ .................. C07D 401/04; C07D 403/04; A61K 31/445; A61K 31/415
[52] U.S. Cl. .................. 514/391; 514/235.8; 514/252; 514/256; 514/278; 514/314; 514/326; 514/361; 514/362; 514/363; 514/365; 514/374; 544/69; 544/139; 544/229; 544/238; 544/242; 544/336; 546/13; 546/19; 546/20; 546/193; 546/210
[58] Field of Search .................. 514/391, 278; 548/301.4, 300.7; 546/19, 20

[56] References Cited

U.S. PATENT DOCUMENTS

| 4,320,135 | 3/1982 | Kathawala | 548/301.4 |
| 4,944,791 | 7/1990 | Schroder et al. | 548/301.4 |
| 5,221,675 | 6/1993 | Chung et al. | 514/278 |

FOREIGN PATENT DOCUMENTS

| 578516 | 1/1994 | European Pat. Off. . | |
| 2139925 | 1/1973 | France . | |
| 2329276 | 5/1977 | France . | |

OTHER PUBLICATIONS

Winters et al. (CA 73:98869) @1970.
Nakanishi et al. (CA 75:110315) @1971.
Nakanishi et al. (Derwent Abstract 44875S–B) Jul. 1971.
Sankyo (Derwent Abstract C90–104571), Sep. 1989.
Torigoshi, et al., "Spirohydantoin Derivatives", Chemical Abstracts, vol. 75, No. 17, Abstract No. 110315n, p. 437, 1971.
Winters, et al, "Synthesis of Spirohydantoins From Basic Heterocyclic Ketones", vol. 73, No. 19, Abstract No. 98869v, p. 368, 1970.
Nakanishi, et al, "Spirohydantoin Compounds", vol. 66, No. 15, Abstract No. 65473p, p. 6157, 1967.

*Primary Examiner*—Robert W. Ramsuer
*Assistant Examiner*—Laura L. Stockton
*Attorney, Agent, or Firm*—Bierman and Muserlian

[57] ABSTRACT

Novel imidazoles of the formula

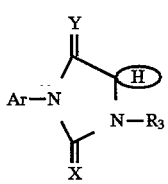

I wherein the substituents are as defined in the disclosure and their non-toxic, pharmaceutically acceptable addition salts with acids and bases having antiandrogenic activity.

3 Claims, No Drawings

METHOD OF INDUCING ANTIANDROGENIC ACTIVITY USING IMIDAZOLIDINES SUBSTITUTED WITH A HETEROCYCLE

STATE OF THE ART

In Japanese Application J 48,087,030, 3-phenyl-2-thio-hydantoins are described which are presented as inhibiting the germination of certain plants. In French Patent No. 2,329,276, imidazolidines are described which are presented as possessing an antiandrogen activity but the products of this patent are different from the products of the present invention.

OBJECTS OF THE INVENTION

It is an object of the invention to provide the novel compounds of formula I and their addition salts and a process and intermediates for their preparation.

It is another object of the invention to provide novel antiandrogenic compositions and a method of inducing antiandrogenic activity in warm-blooded animals, including humans.

These and other objects and advantages of the invention will become obvious from the following detailed description.

THE INVENTION

The novel imidazolidines of the invention are compounds selected from the group consisting of a compound of the formula

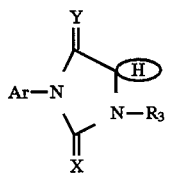

wherein (H) is a saturated heterocyclic with 4 to 7 ring members containing: either an oxygen, nitrogen or optionally oxidized sulfur, the nitrogen being optionally substituted by $R_3$ or two oxygen and optionally one boron atom substituted by phenyl, the heterocycle being optionally substituted on a carbon atom with oxo, at least one alkyl optionally substituted, or cycloalkyl of 4 to 7 members, Ar is aryl optionally substituted by at least one member of the group consisting of i) halogen, cyano, nitro, trifluoromethyl, trifluoromethoxy, hydroxyl, free, salified, esterified or amidified carboxy,

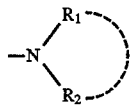

in which the nitrogen atom is optionally oxidized and $R_1$ and $R_2$ are individually selected from the group consisting of hydrogen and optionally substituted alkyl or form together with the nitrogen atom to which they are attached a monocyclic of 5, 6 or 7 ring members or a condensed ring of 8 to 14 ring members, both optionally containing at least one heteroatom selected from the group consisting of oxygen, nitrogen and sulfur, and being optionally substituted, iii) optionally substituted alkyl, alkoxy, alkylthio and arylthio,

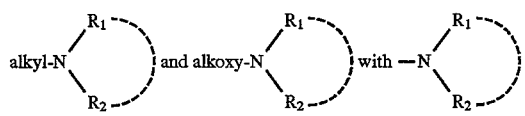

as defined above, x is oxygen or sulfur,

Y is oxygen or sulfur or NH, $R_3$ is selected from the group consisting of hydrogen, aryl and alkyl, alkenyl and alkynyl of up to 6 carbon atoms optionally interrupted by at least one oxygen, nitrogen or optionally oxidized sulfur, all being optionally substituted, the substituents of the ring

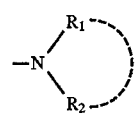

and the alkyl, aryl, alkoxy, alkenyl and alkynyl indicated above as optionally substituted are selected from the group consisting of halogen, optionally salified, esterified or etherified hydroxy, alkoxy, aryloxy, alkyl, haloalkoxy, haloalkyl, mercapto, alkylthio and arylthio in which the sulfur is optionally oxidized, acyl and acyloxy of an organic carboxylic acid of up to 6 carbon atoms, free, salified, esterified or amidified carboxy, cyano, nitro, amino, mono or dialkylamino, aryl and arylalkyl, the last two being optionally substituted by at least one member of the group consisting of halogen, hydroxyl, alkyl and alkoxy of up to 6 carbon atoms, trifluoromethyl, trifluoromethoxy, nitro, cyano, free, salified or esterified carboxy and tetrazolyl, all the sulfurs being optionally oxidized into sulfoxide or sulfone, the said products of formula I being in all the possible racemic, enantiomeric and diastereoisomeric isomer forms and their non-toxic, pharmaceutically acceptable addition salts with acids or bases.

As examples of the saturated heterocycles for H are groups containing one sulfur, oxygen or nitrogen such as

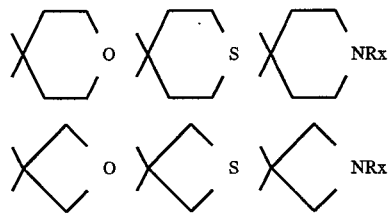

wherein $R_x$ is selected from the values of $R_3$ and especially hydrogen and alkyl optionally interrupted by at least one of oxygen, optionally oxidized sulfur and nitrogen and optionally substituted as indicated herein; groups containing two oxygens and optionally one boron such as

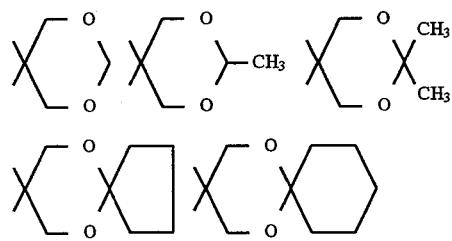

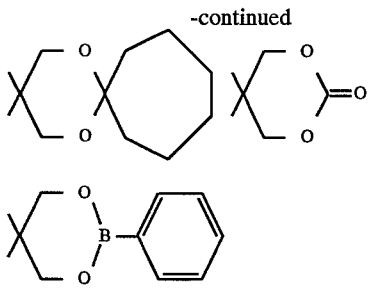

H preferably has 6 members in the ring.

Examples of alkyl of 1 to 12 carbon atoms are methyl, ethyl, propyl, isopropyl, butyl, isobutyl, sec-butyl, tert-butyl, pentyl, isopentyl, sec-pentyl, tert-pentyl, neo-pentyl, hexyl, isohexyl, sec-hexyl, tert-hexyl, heptyl, octyl, decyl, undecyl and dodecyl. Alkyls of 1 to 4 carbon atoms are preferred, i.e. methyl, ethyl, propyl and isopropyl.

Examples of alkenyl of up to 12 carbon atoms are vinyl, allyl, 1-propenyl, butenyl, pentenyl and hexenyl. The alkenyl of up to 4 carbon atoms are preferred such as allyl, propenyl or butenyl.

Examples of alkynyl of up to 12 carbon atoms are ethynyl, propargyl, butynyl, pentynyl and hexynyl, with alkynyl of up to 4 carbon atoms being preferred such as propargyl.

Examples of alkoxy of up to 12 carbon atoms and preferably 4 carbon atoms are preferably methoxy, ethoxy, propoxy or isopropoxy as well as linear, secondary or tertiary butoxy.

Examples of cycloalkyl of up to 12 carbon atoms are cyclopropyl, cyclobutyl and preferably cyclopentyl, cyclohexyl and cycloheptyl.

Examples of aryl are carbocyclic aryls such as phenyl or naphthyl or the monocyclic heterocyclic aryls with 5 or 6 ring members or having condensed rings containing one or more heteroatoms preferably chosen from oxygen, sulfur and nitrogen. Among the heterocyclic aryls with 5 ring members are furyl, thienyl, pyrrolyl, thiazolyl, oxazolyl, imidazolyl, thiadiazolyl, pyrazolyl, isoxazolyl and tetrazolyl. Among the heterocyclic aryls with 6 ring members are pyridyl, pyrimidinyl, pyridazinyl and pyrazinyl. Among the condensed aryls are indolyl, benzofurannyl, benzothienyl and quinolinyl. Phenyl, tetrazolyl and pyridyl are preferred.

Examples of arylalkyls are a combination of alkyl and aryl as mentioned above. Benzyl, phenethyl, pyridylmethyl, pyridylethyl or tetrazolylmethyl are preferred.

Examples of halogen are fluorine, chlorine, bromine or iodine with fluorine, chlorine and bromine being preferred.

Examples of alkyls substituted by one or more halogens or haloalkyl are monofluoro-, chloro-, bromo- or iodomethyl or -ethyl, difluoro-, dichloro- or dibromomethyl and trifluoromethyl. Examples of alkoxys substituted by one or more halogens or haloalkoxy are bromoethoxy, trifluoromethoxy, trifluoroethoxy and pentafluoroethoxy.

Examples of substituted aryl or aralkyl are those in which the phenyl is substituted in ortho, meta or para position by at least one member of the group consisting of fluorine, alkylthio, hydroxy, hydroxyalkyl, alkoxy, trifluoromethyl, trifluoroethyl, pentafluoroethyl and cyano.

Examples of acyl of an organic carboxylic acid of up to 7 carbon atoms are formyl, acetyl, propionyl, butyryl or benzoyl but it can also be valeryl, hexanoyl, acryloyl, crotonoyl or carbamoyl. Examples of acyloxy of an organic carboxylic acid of up to 7 carbon atoms are formyloxy, acetoxy, propionyloxy, butyryloxy or benzoyloxy.

Aryloxy preferably designates the groups in which the aryl is as defined above such as phenoxy. Arylalkoxy preferably designates the groups in which the aryl and the alkoxy represent the groups as defined above such as benzyloxy, phenylethoxy or phenylisopropoxy. Arylthio preferably designates the groups in which the aryl are as defined above such as phenylthio, pyridylthio or pyrimidylthio, imidazolylthio or N-methylimidazolylthio.

Examples of alkylthio are the groups in which the alkyl is as defined above such as methylthio, ethylthio, propylthio, isopropylthio, butylthio, sec-butylthio, tert-butylthio, isopentylthio or isohexylthio; the alkylthio is optionally substituted such as in hydroxymethylthio, aminoethylthio, haloalkylthio such as preferably bromoethylthio, trifluoromethylthio, trifluoroethylthio or pentafluoroethylthio and arylalkylthio such as benzylthio or phenethylthio.

The sulfur atoms can be non-oxidized as in alkylthio, arylthio or can be oxidized to give alkylsulfinyl, arylsulfinyl, alkyl-sulfonyl or arylsulfonyl. Alkylsulfinyl and alkylsufonyl designate the groups in which the alkyl is chosen from the values indicated above for the alkyl such as methylsulfinyl, ethyl-sulfinyl, methylsulfonyl or ethylsulfonyl. Arylsulfinyl and arylsulfonyl designates the arylthios in which the aryl radical is chosen from the values indicated above for the aryl such as phenyl-sulfinyl or -sulfonyl, pyridyl-sulfinyl or -sulfonyl, pyrimidyl-sulfinyl or -sulfonyl, imidazolyl-sulfinyl or -sulfonyl or N-methylimidazolyl-sulfinyl or -sulfonyl.

The carboxys of the products of formula I can be salified, amidified or esterified by the various groups known to a man skilled in the art. Examples of esterified carboxy are alkoxycarbonyl such methoxycarbonyl, ethoxycarbonyl, propoxycarbonyl, n-butyl, tert-butloxy-carbonyl and benzyloxycarbonyl, the alkyls optionally substituted by at least one member selected from the group consisting of halogen, hydroxyl, alkoxy, acyl, acyloxy, alkylthio, amino or aryl such as chloromethyl, hydroxypropyl, propionyloxymethyl, methylthiomethyl, dimethylaminoethyl, benzyl or phenethyl.

There can be mentioned as easily cleavable ester remainders methoxymethyl, ethoxymethyl; acyloxyalkyl such as pivaloyloxymethyl, pivaloyloxyethyl, acetoxymethyl or acetoxyethyl; alkoxycarbonyloxy alkyl such as methoxycarbonyloxymethyl or ethyl, isopropyloxycarbonyloxy methyl or ethyl. A list of such ester radicals can be found in European Patent No. 0,034,536.

Amidified carboxy are groups of the type

Those in which the

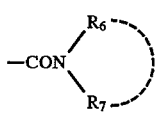

in which $R_6$ and $R_7$ are individually hydrogen or alkyl of 1 to 4 carbon atoms such as methyl, ethyl, propyl, isopropyl, butyl, isobutyl, sec-butyl or tert-butyl.

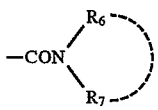

is amino, mono- or dimethylamino, mono- or diethylamino, methylethylamino, monopropylamino or monobutylamino radical are preferred.

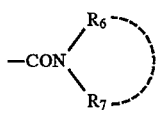

can also be a heterocyclic which may or may not contain an additional heteroatom such as pyrrolyl, imidazolyl, indolyl, piperidino, morpholino, piperazinyl. The piperidino, morpholino or piperazinyl optionally substituted on the second nitrogen atom are preferred such as methylpiperazinyl, fluoromethylpiperazinyl, ethylpiperazinyl, propylpiperazinyl, phenylpiperazinyl or benzylpiperazinyl. In these last two groups, the phenyl and benzyl can be substituted such as chlorophenyl or trifluorophenyl.

Salified carboxy means the salts formed for example with an equivalent of sodium, potassium, lithium, calcium, magnesium or ammonium and the salts formed with organic bases such as methylamine, propylamine, trimethylamine, diethylamine, triethylamine, N,N-dimethylethanolamine, tris(hydroxymethyl) amino methane, ethanolamine, pyridine, picoline, dicyclohexylamine, morpholine, benzylamine, procaine, lysine, arginine, histidine and N-methylglucamine. The sodium salt is preferred.

Examples of heterocyclics containing one or more heteroatoms are saturated monocyclic heterocyclics such as oxirannyl, oxolannyl, dioxolannyl, pyrrolidinyl, imidazolidinyl, pyrazolidinyl, piperidyl, piperazinyl or morpholinyl.

Examples of alkyl, alkenyl, or alkynyl optionally interrupted by a heteroatom chosen from sulfur, oxygen or nitrogen are identical or different in their structure, these heteroatoms obviously not being able to be situated at the end thereof. Examples of alkoxyalkyl are methoxymethyl, methoxyethyl or propyloxypropyl and of alkoxyalkoxyalkyl are methoxyethoxymethyl as well as alkylthioalkyls such as propylthiopropyl, propylthioethyl and methylthiomethyl.

By esterified, etherified or protected hydroxyl is meant

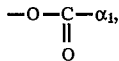

$\alpha_2$—O—$\alpha_3$ or —O—P respectively, formed from a hydroxyl by the usual methods known to one skilled in the art and in which P represents a protective group, $\alpha_1$, $\alpha_2$ and $\alpha_3$ are alkyl, alkenyl, alkynyl, aryl or arylalkyl having up to 12 carbon atoms and optionally substituted as defined above in particular for $R_3$.

Examples of protective group P, as well as the formation of the protected hydroxyl, are given particularly in the standard book of one skilled in the art: Protective Groups in Organic Synthesis, Theordora W. Greene, Harvard University, published in 1981 by Wiley-Interscience Publishers, John Wiley & Sons.

The protection group of the hydroxyl which can be represented by P are selected from the group consisting of for example formyl, acetyl, chloroacetyl, bromoacetyl, dichloroacetyl, trichloroacetyl, trifluoroacetyl, methoxyacetyl, phenoxyacetyl, benzoyl, benzoylformyl and p-nitrobenzoyl. The following groups can also be mentioned: ethoxycarbonyl, methoxycarbonyl, propoxycarbonyl, βββ-trichloro-ethoxycarbonyl, benzyloxycarbonyl, tert-butoxycarbonyl, 1-cyclo propylethoxycarbonyl, tetrahydro-pyrannyl, tetrahydrothiopyrannyl, methoxytetrahydropyrannyl, trityl, benzyl, 4-methoxybenzyl, benzhydryl, trichloroethyl, 1-methyl 1-methoxyethyl, phthaloyl, propionyl, butyryl, isobutyryl, valeryl, isovaleryl, oxalyl, succinyl and pivaloyl, phenylacetyl, phenylpropionyl, mesyl, chlorobenzoyl, para-nitrobenzoyl, para-tert-butylbenzoyl, caprylyl, acryloyl, methylcarbamoyl, phenylcarbamoyl and naphthylcarbamoyl.

P can preferably be

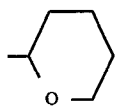

or a silicon derivative such as trimethylsilyl.

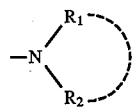

which represents an amino, monoalkylamino, dialkylamino or heterocycle can be chosen from the values defined above for

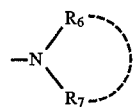

The

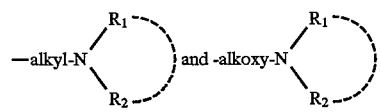

are such that in these radicals, alkyl, alkoxy and

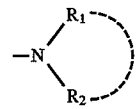

have the values indicated above, such as N,N-dimethylaminomethyl or N,N-dimethylaminomethoxy.

The amino and particularly

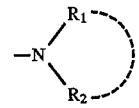

also designates the amino substituted by one or two alkyls chosen from the alkyls as defined above themselves substituted as indicated above, particularly by one or more halogen, hydroxyl, alkoxy, cyano, free, salified, esterified or amidified carboxy, such as hydroxyalkyl, cyanoalkyl and carboxyalkyl.

When the products of formula I as defined above contain an amino salified by an acid, it is understood that these acid salts are also a subject of the invention.

The addition salts with non-toxic, pharmaceutically acceptable mineral or organic acids of the products of formula I can be, for example, the salts formed with the following acids: hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acid such as methanesulfonic acid, ethanesulfonic acid, propanesulfonic acid, alkyldisulfonic acid such as methanedisulfonic acid, α,β-ethanedisulfonic acid, arylmonosulfonic acids such as benzenesulfonic acid and aryldisulfonic acids. Preferred are the salts formed with hydrochloric acid methanesulfonic acid.

Preferred products of formula I are those wherein (H) is

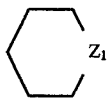

in which $Z_1$ is oxygen, sulfur optionally oxidized in the form of sulfoxide or sulfone or —N—$R_4$ in which $R_4$ is chosen from hydrogen, alkyl, alkylphenyl and phenyl optionally substituted by at least one halogen, hydroxy, alkoxy, free, salified, esterified or amidified carboxy and phenyl optionally substituted by at least one member of the group consisting of halogen, hydroxyl, alkyl, alkoxy, trifluoromethyl, trifluoromethoxy, nitro, cyano and free, salified or esterified carboxy and

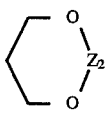

in which $Z_2$ is either —CH$_2$— optionally substituted by one or two alkyls, cycloalkyl of 3 to 7 carbon atoms or oxo or boron substituted by phenyl, Ar is aryl optionally substituted by at least one member of the group consisting of halogen, cyano, nitro, trifluoromethyl, trifluoromethoxy, hydroxyl, free, salified, esterified or amidified carboxy, alkyl, alkoxy, alkylthio, arylthio, amino, mono or dialkylamino, aminoalkyl, mono or dialkylaminoalkyl, aminoalkoxy, mono or dialkylaminoalkoxy, pyrrolidinyl, piperidyl, morpholino and piperazinyl optionally substituted on the second nitrogen atom by alkyl, phenylalkyl, alkylphenyl or phenyl, the phenyl optionally substituted by at least one halogen, hydroxyl or alkoxy, X is oxygen or sulfur, Y is oxygen or sulfur or NH, $R_3$ is selected from the group consisting of hydrogen, aryl and alkyl, alkenyl and alkynyl optionally interrupted by one or more oxygen, nitrogen or optionally oxidized sulfur, all being optionally substituted by at least one member of the group consisting of halogen, optionally salified, esterified or etherified hydroxy, alkoxy, aryloxy, alkyl, trifluoromethyl, trifluoromethoxy, free, salified, esterified or amidified carboxy, cyano, nitro, amino, mono or dialkylamino, phenyl, benzyl and phenethyl, the phenyls optionally substituted by at least one member of the group consisting of halogen, hydroxyl, alkyl, alkoxy, cyano, nitro and trifluoromethyl, the said products of formula I being in all the possible racemic, enantiomeric and diastereoisomeric isomer forms, as well as their addition salts with mineral and organic acids or with mineral and organic bases.

Among the preferred compounds of formula I are those wherein Ar is phenyl or pyridyl optionally substituted as above, those of the formula

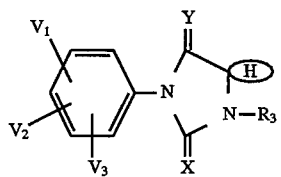

wherein (H) is either

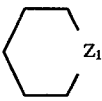

in which $Z_1$ is oxygen, sulfur optionally oxidized in the form of the sulfoxide or sulfone or —N—$R_4$ in which $R_4$ is hydrogen or alkyl optionally substituted by one or more radicals chosen from halogen, hydroxy, alkoxy or free, salified, esterified or amidified carboxy or (H) is

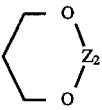

in which $Z_2$ is either a —CH$_2$— optionally substituted by one or two alkyls, cycloalkyl of 4 to 7 carbon atoms or oxo, or boron substituted by phenyl, $W_1$, $W_2$ and $W_3$ are individually selected from the group consisting of hydrogen, halogen, hydroxyl, alkoxy, cyano, amino, mono or dialkylamino, nitro, trifluoromethyl, free, esterified, amidified or salified carboxy, alkylthio and arylthio, $R_3$ is hydrogen or alkyl optionally substituted by at least one member of the group consisting of halogen, optionally salified or etherified hydroxy, alkoxy and free, esterified, amidified or salified carboxy, X is oxygen or sulfur, Y is oxygen or NH, the said products of formula F being in all the possible racemic, enantiomeric and diastereoisomeric isomer forms, as well as their addition salts with mineral and organic acids or with mineral and organic bases.

Among the specific preferred products of the invention are 4-(2,4-dioxo-1-(4-hydroxybutyl)-8-oxa-1,3-diazaspiro (4.5)decan-3-yl)-2-(trifluoromethyl)-benzonitrile, 4-(2,4-dioxo-1-(2-fluoroethyl)-8-oxa1,3-diazaspiro (4.5)decan-3-yl)-2-(trifluoromethyl)-benzonitrile, 3-(4-cyano-3-(trifluoromethyl)-phenyl)-2,4-dioxo-8-oxa1,3-diazaspiro (4.5)decane-1-acetonitrile and 4-(2,4-dioxo-1-(4-hydroxybutyl)-8-thia-1,3-diazaspiro (4.5)decan-3-yl)-2-(trifluoromethyl)-benzonitrile.

The novel process of the invention for the preparation of the compounds of formula I comprises reacting a compound of the formula $$Ar—N=C=X \qquad \text{II}$$

in which X and Ar have the meaning above in which the optional reactive functions are optionally protected in the presence of a tertiary base either with a product of the formula

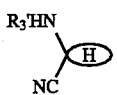

in which (H) has the meaning above and $R'_3$ has the meaning above for $R_3$ in which the optional reactive functions are optionally protected to obtain a product of the formula

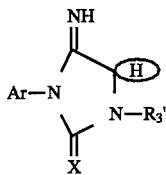    Ia in which Ar, (H) and $R'_3$ have the meanings above, or with a product of the formula

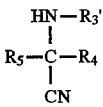    X in which $R'_3$ has the meaning above and $R_4$ and $R_5$ are individually hydroxyalkyl in which the hydroxy function is optionally protected to obtain, optionally after deprotection of the hydroxyl, a diol of the formula

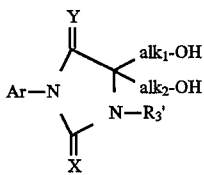    IV in which Ar Y, X and $R'_3$ have the meanings above, and $alk_1$ and $alk_2$ are individually alkyl, the product of formula IV is reacted: either with a compound of the formula

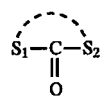    V in which $S_1$ and $S_2$ are individually hydrogen or alkyl optionally substituted, or $S_1$ and $S_2$ form together with C=O a cycloalkanone of 4 to 7 members to obtain a product of the formula

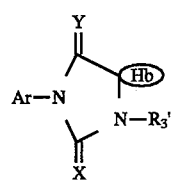    Ib in which (Hb) is a saturated heterocycle with 4 to 7 members containing two oxygen atoms and optionally substituted by cycloalkyl or by one or two alkyls optionally substituted, or with phosgene or a derivative of phosgene or N,N'-carbonyldiimidazole to obtain a product of the formula

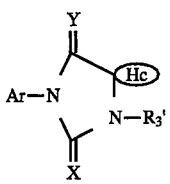    Ic in which Ar, Y, X and $R'_3$ have the meanings above and (Hc) is a saturated heterocycle of 4 to 7 ring members containing two oxygen and substituted on a carbon atom by oxo, or with the compound of the formula

$$R-B(OH)_2 \quad VI$$

in which R is phenyl to obtain a product of the formula

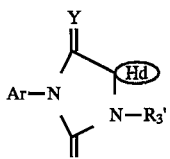    Id in which Ar, Y, X and $R'_3$ have the meanings above and (Hd) is a saturated heterocycle with 4 to 7 ring members containing two oxygen and one boron substituted by phenyl, the hydroxyls of which product of formula IV can optionally be protected to obtain a product of formula IV', which products of formulae Ia, Ib, Ic, Id, and IV' as defined above, if appropriate, and if necessary or if desired, can be subjected to any one or more of the following reactions in any order:

a) elimination reaction of the optional protective groups which can be carried by $R'_3$, then if appropriate the action of an esterification, amidification or salification agent, b) hydrolysis reaction of the >C=NH group into a carbonyl function, c) conversion of the >C=O into a >C=S, d) conversion of the >C=S into >C=O, e) when $R'_3$ is alkoxyalkyl, conversion reaction of R' into hydroxylalkyl, f) when $R'_3$ is hydrogen, the action of a reagent of formula Hal-$R''_3$ in which $R''_3$ has the values of $R'_3$ with the exception of hydrogen and Hal is halogen to obtain products of the formulae Ia, Ib, Ic, Id and IV' as defined above, in which $R''_3$ has the meaning indicated previously, g) if desired, the action on the products obtained in f, of an elimination agent of the optional protective groups which can be carried by $R''_3$ or if appropriate, the action of an esterification, amidification or salification agent, which products of formulae Ib and IV' as defined above can be subjected to the reaction indicated above in f), then hydrolyzed into a product of the formula

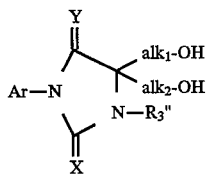    VII in which Ar, X, Y, $alk_1$, $alk_2$ and $R''_3$ have the meanings above, which can be subjected to the same reactions as the product of formula IV as defined above to obtain the corresponding products of formula Ib, Ic, or Id in which $R''_3$ has the meaning indicated above, which products of formulae Ia, IV, IV', VII, Ib, Ic and Id as defined above, if appropriate, and if necessary or if desired, can be subjected to any one or more of the following reactions in any order:

salification by a mineral or organic acid or by a base to obtain the corresponding salt, elimination reaction of the optional protective groups which can be carried by the protected reactive functions.

The reaction of the products of formula II with the products of formulae III or X is preferably carried out in an organic solvent such as tetrahydrofuran or dichloroethane but ethyl ether or isopropyl ether can also be used. The operation is carried out in the presence of a tertiary base such as triethylamine or also pyridine or methylethylpyridine.

The reaction of the product of formula IV with a compound of formula V to give a product of formula Ib, can be carried out by the usual conditions known to one skilled in the art and particularly as indicated in the book by Greene "Protection Group in Organic Synthesis" whose reference is given above.

When $S_1$ and $S_2$ both are hydrogen, the reaction is particularly described in the publication Hough et al., J. Chem. Soc., p. 1525 (1952). One of $S_1$ and $S_2$ can particularly be hydrogen or methyl or tert-butyl and other can particularly be methyl.

$S_1$ and $S_2$ can also formwith C=O a cycloalkanone such as cyclopentanone, cyclohexanone or cycloheptanone. The reaction of such compounds of formula V with the product of formula IV as defined above is particuarly described by van Heeswijk et al. Carbohydr. Res., Vol. 58, p. 337 (1977).

The product of formula Ic as defined above from the product of formula IV as defined above, can be carried out by reaction with phosgene or a derivative such as triphosgene or N,N'-carbonyldiimidazole, as described by Haworth et al., J. Chem. Soc., Vol. 151 (1930); Letsinger et al., J. Org. Chem., Vol. 32, p. 296 (1967); Kutney et al., Synth. Common., Vol. 5, p. 47 (1975).

The product of formula Id as defined above by reaction of the product of formula IV with the product of formula VI can be carried out as indicated by Ferrier, Methods Carbohydr. Chem., Vol. VI, pp. 419–426 (1972).

The two hydroxyls of the product of formula IV as defined above can be protected to obtain the product of formula IV' as defined above, particularly by the action of dihydropyran or a chlorosilane such as terbutyldimethylsilyl chloride.

The optional reactive functions of $R_3$ and which are optionally protected, are hydroxy or amino functions. The usual protective groups are used to protect these functions such as the protective groups of the amino i.e. tert-butyl, tert-amyl, trichloroacetyl, chloroacetyl, benzyhydryl, trityl, formyl and benzyloxycarbonyl. As a protective group of the hydroxy, there are formyl, chloroacetyl, tetrahydropyrannyl, trimethylsilyl and tert-butyl dimethylsilyl.

It is understood that the above list is not limitative and that other protective groups, for example known in the chemistry of peptides, can be used. A list of such protective groups is found for example in French Patent No. 2,499,995, the content of which is incorporated here by way of reference. The optional elimination reactions of the protective groups are carried out as indicated in U.S. Pat. No. 2,499,995. The preferred method of elimination is acid hydrolysis using acids chosen from hydrochloric acid, benzene sulfonic acid or p-toluene sulfonic acid, formic acid, or trifluoroacetic acid. Hydrochloric acid is preferred.

The optional hydrolysis reaction of the >C=NH into a ketone is also preferably carried out using an acid such as aqueous hydrochloric acid at reflux. When the hydrolysis of the >C=NH into carbonyl is carried out on a molecule also containing >C=S, this can be converted into >C=O. The free OH which can optionally be contained by $R_3$ can then be converted into SH.

The conversion reaction of >C=O into >C=S is carried out using a so-called Lawesson reagent of the formula

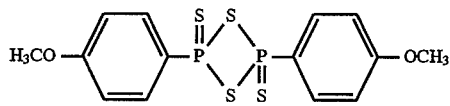

which is a product marketed by the FLUKA company and the use of which is described in Bull. Soc. Chim. Belg., Vol. 87, No. 3, (1987), p. 229.

When it is desired to convert two >C=O into two >C=S, the operation is carried out in the presence of an excess of Lawesson reagent. This is also the case when one starts with a molecule containing >C=S and >C=O and it is desired to convert the said >C=O into a >C=S.

On the other hand, when one starts with a molecule containing two >C=O and it is desired to obtain a product containing only one >C=S, the operation is carried out in the presence of a deficit of Lawesson reagent. A mixture of three products is then generally obtained: each of the two products containing a >C=O and a >C=S and a product containing two >C=S. These products can then be separated by the usual methods such as chromatography.

The action on the products of formula Ia, Ib, Ic, Id or IV' of the reagent of formula Hal-R"$_3$ is carried out in the presence of a strong base such as sodium or potassium hydride. The operation can be carried out by phase transfer reaction in the presence of quaternary ammonium salts such as tert-butyl ammonium. The protective groups which can be carried by R"$_3$ can be for example one of those previously mentioned for $R_3$. The elimination reactions of the protective groups is carried out under the conditions indicated above.

The elimination of the terbutyldimethylsilyl group can be carried out for example using hydrochloric acid. The optional esterification of the products of formula I, in which R"$_3$ has a free OH is carried out under standard conditions. There can be used for example an acid or a functional derivative, for example an anhydride such as acetic anhydride in the presence of a base such as pyridine.

The optional esterification or salification of the products of formula I in which R"$_3$ is COOH is carried out under standard conditions known to one skilled in the art. The optional amidification of the products of formula I in which R"$_3$ has a COOH is carried out under standard conditions. A primary or secondary amine can be used on a functional derivative of the acid for example a symmetrical or mixed anhydride.

Also a subject of the invention is a preparation for the products of the formula

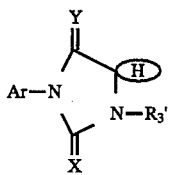

in which Ar, X, Y, R'$_3$ and (H) have the meanings above, characterized in that a product of the formula Ar—Hal  VIII in which Ar has the previous meaning and Hal is halogen is reacted with a product of the formula

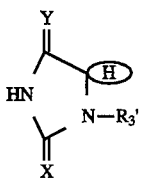

IX in which X, Y, R'₃ and (H) have the meanings above, the reaction being carried out in the presence of a catalyst and optionally of a solvent.

As far as the products of formula VIII are concerned, Hal preferably is chlorine, but can be bromine or iodine. The role of the catalyst is probably to trap the hydrogen halide which is released and to facilitate the condensation reaction of the product of formula VIII with the product of formula IX to give the desired product.

A more particular subject of the invention is a process as defined above in which the catalyst is a metal in native or oxidized form or a base. When the catalyst used is a metal, this metal can be copper or nickel and it can be in native form, in the form of metallic oxide or in the form of metallic salts. The metallic salts can be chloride or acetate.

When the catalyst is a base, this base can be for example sodium hydroxide or potassium hydroxide and if desired, dimethylsulfoxide can be added to the reaction medium.

A more particular subject of the invention is a process in which the catalyst is selected from cuprous oxide, cupric oxide, copper in native form and a base such as sodium hydroxide or potassium hydroxide. The copper in native form used as catalyst is preferably in the form of a powder. Preferably, the catalyst is cuprous oxide.

The solvent used is preferably selected from ethers with a high boiling point such as phenyl oxide, diglyme, triglyme and dimethylsulfoxide but can be an oil with a high boiling point such as paraffin or vaseline. The process is preferably carried out in the presence of a solvent of ether type such as phenyl oxide, diglyme, triglyme or dimethylsulfoxide, most preferably phenyl oxide or triglyme.

The preparation of the desired product defined above can be carried out under pressure or at atmospheric pressure, preferably at a high temperature and the reaction is carried out at a temperature greater than 100° C., preferably greater than 150° C. for more than 2 hours.

A very particular subject of the invention is that the reaction is carried out in the presence of cuprous oxide in triglyme at a temperature greater than or equal to 200° C. and for more than 3 hours.

The antiandrogenic compositions of the invention are comprised of an antiandrogenically effective amount of at least one compound of formula I or its non-toxic, pharmaceutically acceptable addition salts with an acid or base and an inert pharmaceutical carrier. The compositions may be in the forms of solutions or injectable suspensions, tablets, coated tablets, capsules, syrups, suppositories, creams, ointments, gels and lotions and in the form of liposomes prepared by known methods.

Examples of the carrier or excipient are aqueous or non-aqueous vehicles, talc, gum arabic, lactose, starch, magnesium stearate, cocoa butter, fatty substances of animal or vegetable origin, paraffin derivatives, glycols, various wetting, dispersing or emulsifying agents and preservatives.

The compositions have an antiandrogenic activity as they fix on the androgen receptor and are useful in the treatment of adenomas and neoplasias of the prostate as well as benign hypertrophy of the prostate, on their own or in combination with analogs of LHRH. They can also be used in the treatment of benign or malignant tumors possessing androgen receptors and more particularly cancers of the breast, the skin, the ovaries, the bladder, the lymphatic system, the kidney and the liver and for the treatment of cutaneous diseases such as acne, hyperseborrhoea, alopecia or histutism.

The composition can therefore be used in dermatology on their own or in combination with antibiotics such as the derivatives of azelaic and fusidic acids, erythromycin, as well as derivatives of retinoic acid or an inhibitor of 5-reductase such as (5α, 17β)-1,1-dimethylethyl 3-oxo 4-aza-androst-1-ene 17-carboxamide (or Finasteride, Merck 11th ed.) for the treatment of acne, alopecia or hirsutism. They can also be combined with a product stimulating hair growth such as Minoxidil for the treatment of alopecia.

The compositions can also be used in the veterinary field for the treatment of behavioral disorders such as aggressiveness, androgen-dependent disease such as circum analum in dogs and tumors having androgen receptors. They can also be used to cause a chemical castration in animals. When the products of formula I are in radioactive form (tritium, carbon 14, iodine 125 or fluorine 18), the compositions can also be used as specific labels for the androgen receptor and can be used in diagnostics in medical imagery.

The novel method of the invention for inducing antiandrogenic activity in warm-blooded animals, including humans, comprises administering to warm-blooded animals an antiandrogencially effective amount of a compound of formula I or its non-toxic, pharmaceutically acceptable salts with acids or bases. The compounds may be administered parenterally, buccally, perlingually, rectally or topically. The usual daily dose is 0.15 to 6.5 mg/kg depending on the specific compound, the condition treated and the method of administration.

The starting compounds of formula II are prepared by reacting a compound of the formula $$Ar—NH_2 \qquad (A)$$

with phosgene when X is oxygen or thiophosgene when X is sulfur as described in European Patent No. 0,494,819. French Patent No. 2,329,276 describes the compounds when Ar is phenyl. The amines of formula A are described in European Patent No. 0,002,892 and French Patent No. 2,142,804.

The products of formula X are known or can be prepared from the corresponding cyanhydrin by the process described in J. Am. Chem. Soc. (1953), Vol. 75, p. 4841, BEIL I, Vol. 4, p. 526 or J. Org. Chem. Vol. 27, p. 2901 (1962). The products of formula X in which R'₃ is other than hydrogen can be obtained by the action of a product of formula R"₃ Hal on 2-cyano-2-amino-propane under the conditions stated above for the action of R"₃ Hal on the products of formula Ia. An example of a preparation of this type is described in Jilek et al., Collect. Czech. Chem. Comm., Vol. 54(8), p. 2248 (1989).

The products of formulae VIII and IX for obtaining products of formula I' are known and commercially available or can be prepared by methods known to one skilled in the art.

The preparation of the products of formula IX is described particularly in Zhur. Preklad. Khim., Vol. 28, pp. 969–975 (1955), (CA, Vol. 50, p. 4881a, 1956), Tetrahedron, Vol. 43, p. 1753 (1987), J. Org. Chem., Vol. 52, p. 2407 (1987), Zh. Org. Khim., Vol. 21, p. 2006 (1985), J. Fluor. Chem., Vol. 17, p. 345 (1981) or German DRP No. 637,318 (1935), European Patent No. 0,130,875 and Japanese Patent No. 81,121,524.

The products of formula IX which are derivatives of hydantoin are widely used and mentioned in the literature such as J. Pharm. Pharmacol., No. 67, Vol. 19(4), pp. 209–216 (1967), Khim, Farm. Zh., No. 67, Vol. 1(5), pp 51–52. German Patent No. 2,217,914, European Patent No. 0,091,596 and J. Chem. Soc. Perkin. Trans., Vol. 1, pp 219–221 (1974).

The products of formula III are commercially available such as those used in the preparation of the examples described hereafter. There can be mentioned 4-amino-tetrahydro-2H-pyran-4-carbonitrile, 4-amino-tetrahydro-2H-thiopyran-4-carbonitrile and 4-amino-1-methyl-piperidine 4-carbonitrile.

Also as new industrial products are those of formulae IV and IX in which Ar has the meaning indicated above with the exception of phenyl substituted by two halogens or cyano, nitro, trifluoromethyl or free, salified, amidified or esterified carboxy.

In the following examples, there are described several preferred embodiments to illustrate the invention. However, it should be understood that the invention is not intended to be limited to the specific embodiments.

EXAMPLE 1

4-(4-imino-2-oxo-8-oxa-1,3-diazaspiro[4.5]decan-3-yl)-2-(trifluoromethyl)-benzonitrile

STAGE 1

4-amino-tetrahydro-2H-pyran-4-carbonitrile 8 ml of ammonium hydroxide, 1.58 g of ammonium chloride and 1.23 g of sodium cyanide were successively introduced and the solution obtained was cooled in an ice/methanol bath at about −7° C. 2 ml of tetrahydro-4H-pyran-4-one were added at a temperature of ≦0° C., and the reaction medium was allowed to rise to ambient temperature with vigorous stirring for 18 hours. After extracting 3 times with methylene chloride, washing with salt water and drying, 2.49 g of the expected product (translucent crystals) melting at approximately 46°–47° C. were obtained.

| I.R.: | $(CHCl_3)$ cm$^{-1}$ |
|---|---|
| $NH_2$ | 3390–3374–3324 |
| C≡N | 2225 |
| $NH_2$ def. | 1605 |

STAGE 2

4-(4-imino-2-oxo-8-oxa-1,3-diazaspiro[4.5]decan-3-yl)-2-(trifluoromethyl)-benzonitrile 883 mg of the product of Stage 1 were introduced into 7 ml of 1,2-dichloroethane and 0.3 ml of triethylamine. 6.4 ml of the product obtained in the preparation of Example 7 of European Patent Application EP 0,494,819 were cooled to about −7° C. and added dropwise over 15 minutes. Then, the mixture was allowed to return to ambient temperature and the reaction medium stood for one hour, was evaporated to dryness and purified on silica with methylene chloride-acetone: 7/1 as eluant to obtain 1.85 g of the expected product (white crystals) melting at 249°–250° C.

| I.R.: | (nujol) cm$^{-1}$ |
|---|---|
| OH/NH | 3340–3295 |
| C≡N | 2240 |
| C=O | 1750 |
| Conjugated system aromatic | 1678–1612–1572–1508 |

EXAMPLE 2

4-(2,4-dioxo-8-oxa-1,3-diazaspiro[4.5]decan-3-yl)-2-(trifluoromethyl)-benzonitrile 1.66 g of the product of Example 1 were introduced into 30 ml of methanol, 10 ml of chloroform and 10 ml of 2N hydrochloric acid, and the mixture was refluxed for 50 minutes. 100 ml of water were added and extraction was carried out 3 times with ethyl acetate. The organic phase was washed with salt water, dried and purified on silica with methylene chloride-acetone: 85–15 as eluant. The resultant product was dissolved in 100 ml of isopropanol at about 70° C. and filtration was carried out, followed by concentrating, ice-cooling for one hour, separating and drying to obtain 1,425 g of the expected product (white crystals) melting at 192°–193° C.

| I.R.: | (nujol) cm$^{-1}$ |
|---|---|
| C≡N | 2240 |
| C=O | 1790–1732 |
| Aromatics | 1614–1582–1506 |

EXAMPLE 3

4-(2,4-dioxo-1-(4-hydroxybutyl)-8-oxa-1,3-diazaspiro[4.5]decan-3-yl)-2-(trifluoromethyl)-benzonitrile 55 mg of 50% sodium hydride were introduced and 340 mg of the product of Example 2 and 25 ml of dimethylsulfoxide were added dropwise over 25 minutes. Rinsing was carried out with 0,5 ml of dimethylsulfoxide and 20 minutes after the release of hydrogen had stopped, 0.41 g of 4-iodobutoxy-trimethyl-silane was added. The mixture was allowed to react for 18 hours at ambient temperature and the reaction medium was then poured into 10 ml of water. Extraction was carried out 4 times with ether and the organic phase was washed with water, then with salt water, dried and taken up in a mixture of 10 ml of methanol and 1 ml of 2N hydrochloric acid. After 30 minutes, the mixture was poured into 20 ml of saturated sodium chloride solution and extraction was carried out 3 times with chloroform, followed by drying. Purification was carried out on silica with methylene chloride-acetone 8–2 as eluant to obtain 369 mg of the expected product (friable white foam).

| I.R.: | $(CHCl_3)$ cm$^{-1}$ |
|---|---|
| OH | 3626–3485 |
| C≡N | 2235 |
| C=O | 1775–1721 |
| Aromatics | 1615–1602–1577–1505 |

EXAMPLE 4

4-(2,4-dioxo-1-(2-hydroxyethyl)-8-oxa-1,3-diazaspiro[4.5]decan-3-yl)-2-(trifluoromethyl)-benzonitrile 82 mg of 50% sodium hydride, 510 mg of the product of Example 2 and 4 ml of dimethylsulfoxide were mixed together and rinsed with 0.5 ml of dimethylsulfoxide. 20 minutes after the release of hydrogen had stopped, 572 mg of 2-iodoethoxy-dimethylbutyl-silane were added all at once and the solution was taken to 40° C. for 90 minutes, then to ambient temperature for 18 hours. The reaction medium was poured into 40 ml of water containing 0.2 g of monopotassium phosphate and extraction was carried out 4 times with ether. The extracts were washed with water, then with salt water and dried. Purification was carried out on silica with methylene chloride-ethyl acetate as eluant and the residue was taken up in 16 ml of methanol and 3 ml of 2N hydrochloric acid. Heating to 40° C. was carried out for 40 minutes and the mixture was poured into 50 ml of 50% sodium bicarbonate. Extraction was carried out 3 times with chloroform and the extracts were washed with salt water and dried. Purification on silica was carried out with methylene chloride-acetone 8–2 as eluant to obtain 451 mg of the expected product (white crystals) melting at 196°–197° C.

| I.R.: | (nujol) cm$^{-1}$ |
|---|---|
| OH/NH | 3450 |
| C≡N | 2240 |
| >=O | 1775–1718 |
| Aromatics | 1615–1576–1508 |

EXAMPLE 5

4-(2,4-dioxo-1-(3-hydroxypropyl)-8-oxa-1,3-diazaspiro[4.5]decan-3-yl)-2-(trifluoromethyl)-benzonitrile Using the procedure of Example 4, 109 mg of 50% sodium hydride, 510 mg of the product of Example 2 and 4 ml of dimethyl-sulfoxide were reacted and rinsing was carried out with 0.5 ml of dimethylsulfoxide. Then, 20 minutes after the release of hydrogen had stopped, 1.004 g of 3-bromopropoxydiphenyl-tert-butyl-silane were added and the solution was heated to about 50° C. Proceeding as in Example 4, the solution was taken up in 30 ml of methanol, 10 ml of 2N hydrochloric acid, 10 ml of chloroform and refluxed. After purification on silica with methylene chloride-acetone: 8–2 as eluant, 441 mg of the expected product (white crystals) melting at 155°–156° C. were obtained.

| I.R.: | (nujol) cm$^{-1}$ |
|---|---|
| General adsorption NH/OH | |
| C≡N | 2240 |
| >=O | 1778–1714 |
| Aromatics | 1618–1580–1539–1511 |

EXAMPLE 6

Ethyl 3-(4-cyano-3-(trifluoromethyl)-phenyl)-2,4-dioxo-8-oxa-1,3-diazaspiro[4.5]decan-1-butanoate Using the procedure of Example 3, 123 mg of 50% sodium hydride, 510 mg of the product of Example 2 and 3.5 ml of dimethylsulfoxide were reacted and rinsed with 0.5 ml of dimethylsulfoxide. 15 minutes after the release of hydrogen had stopped, 454 mg of ethyl 4-bromobutyrate were added and the solution was heated to 40° C. for 50 minutes. It was poured into 40 ml of water containing 0.4 g of monopotassium phosphate and extraction was carried out 4 times with ether. The organic phase was washed with water, then with salt water, dried and purified on silica with methylene chloride-ethyl acetate: 85-15 as eluant to obtain 584 mg of the expected product (white crystals) melting at 129°–130° C.

| I.R.: | (CHCl$_3$) cm$^{-1}$ |
|---|---|
| C≡N | 2230 |
| >=O | 1776–1722 |
| Aromatics | 1614–1575–1505 |

EXAMPLE 7

3-(4-cyano-3-(trifluoromethyl)-phenyl)-2,4-dioxo-8-oxa-1,3-diazaspiro[4.5]decan-1-butanoic acid 522 mg of the product of Example 6 and 20 ml of methanol were mixed together and the solution was heated to 30° C., then returned to ambient temperatures 2 ml of 2N sodium hydroxide were added and the reaction medium stood for 4 hours and 30 minutes, then was poured into 30 ml of water and adjusted to pH 2–3. Extraction was carried out 3 times with ethyl acetate and the organic phase was washed with water, then with salt water, dried and purified on silica with methylene chloride-methanol: 9-1 as eluant. Then, solidification was carried out by trituration in 0.2 ml of isopropanol and 5 ml of ether to obtain 345 mg of the expected product (white crystals) melting at 151°–152° C.

| I.R.: | (nujol) cm$^{-1}$ |
|---|---|
| Complex adsorption NH/OH | |
| C≡N | 2240 |
| >=O | 1780–1720 |
| Aromatics | 1615–1581–1510 |

EXAMPLE 8

3-(4-methoxyphenyl)-8-oxa-1,3-diazaspiro[4.5]-decane-2,4-dione

Using the procedure of Stage 2 of Example 1, 380 mg of the product of Stage 1 of Example 1, 4 ml of 1,2-dichloroethane and 0.25 mg of triethylamine were reacted and after bringing to −5° C., then 450 mg of 4-methoxyphenyl isocyanate were added dropwise, followed by rinsing with 1 ml of 1,2-dichloroethane and leaving the reaction medium to rise to ambient temperature. After one hour, separation was carried out, followed by drying. Then, the product was taken up in 20 ml of methanol and 6 ml of chloroform, 6 ml of 2N hydrochloric acid. The solution was refluxed for 2 hours and the solution was concentrated. The concentrate was taken up in 30 ml of water and extraction was carried out 5 times with ethyl acetate. The organic phase was washed with 50% sodium bicarbonate, then with salt water, dried and purified on silica with methylene chloride-acetone: 85–15 as eluant to obtain 493 mg of the expected product (white crystals) melting at 253°–254° C.

| I.R.: | (nujol) cm$^{-1}$ |
|---|---|
| Adsorption region OH/NH | |
| C=O | 1774–1715 |
| Aromatics | 1609–1590–1518 |

EXAMPLE 9

4-(2,4-dioxo-1-(2-fluoroethyl)-8-oxa-1,3-diazaspiro[4.5]decan-3-yl)-2-(trifluoromethyl)-benzonitrile 55 mg of 50% sodium hydride were introduced and 340 mg of the product of Example 2 and 3 ml of dimethylsulfoxide were added drop-wise over about 20 minutes. The solution was rinsed with 0.2 ml of dimethylsulfoxide and 20 minutes after the release of hydrogen had stopped, 0.1 ml of 1-bromo-2-fluoroethane were added. The mixture was heated at 50° C. for 80 minutes and the reaction medium was poured into 10 ml of ice-cooled water containing 0.2 g of monopotassium phosphate. Extraction was carried out 5 times with ether and the organic phase was washed with water, then with salt water and dried. The residue was purified on silica with methylene chloride-acetone: 85–15 as eluant, followed by drying and crystallizing from isopropanol to obtain 281 mg of the expected product (white crystals) melting at 192°–193° C.

| I.R.: | (CHCl$_3$) cm$^{-1}$ |
|---|---|
| C=O | 1777–1723 |
| C≡N | 2238 |
| Aromatics | 1616–1576–1505 |

EXAMPLE 10

3-(4-cyano-3-(trifluoromethyl)-phenyl)-2,4-dioxo-8-oxa-1,3-diazaspiro[4.5]decan-1-acetonitrile 55 mg of 50% sodium hydride were introduced and 340 mg of the product of Example 2 and 2.5 ml of dimethylsulfoxide were added dropwise over 20 minutes. The reaction medium was rinsed with 0.5 ml of dimethylsulfoxide and 15 minutes after the release of hydrogen had stopped, 0.1 ml of bromoacetonitrile was added. The reaction medium stood for one hour and was poured into 15 ml of water containing about 0.3 g of monopotassium phosphate. Extraction was carried out 3 times with ethyl acetate and the extracts were washed with water, then with salt water, dried and purified on silica with methylene chloride-acetone 85–15 as eluant. The resin was dissolved in a mixture of 15 ml of methylene chloride and 30 ml of isopropanol at about 40° C. and concentration was carried out until crystallization occurred to obtain 267 mg of the expected product (white crystals) melting at 210°–211° C.

| I.R.: | (nujol) cm$^{-1}$ |
|---|---|
| C≡N | 2238 |
| >=O | 1782–1730 |
| Aromatics | 1612–1570–1504 |

EXAMPLE 11

3-(4-methylthiophenyl)-8-oxa-1,3-diazaspiro[4.5]-decan-2,4-dione

Using the procedure of Example 8, 380 mg of 4-methylthio-phenylisocyanate, 4 ml of 1,2-dichloroethane and 0.15 ml of triethylamine were reacted to obtain 513 mg of the expected product melting at 256°–257° C.

| I.R.: | (nujol) cm$^{-1}$ |
|---|---|
| Adsorption region OH/NH | |
| >=O | 1776–1720 |
| Aromatics | 1500 |

EXAMPLE 12

4-(4-imino-2-oxo-8-thia-1,3-diazaspiro[4.5]-decan-3-yl)-2-(trifluoromethyl)-benzonltrile

STAGE 1

4-amino-tetrahydro-2H-thiopyran-4-carbonitrile

Using the procedure of Stage 1 of Example 1, 8 ml of ammonium hydroxide, 1.58 g of ammonium chloride, 1.23 g of sodium cyanide and 2.51 g of tetrahydro-4H-thiopyran-4-one were reacted and the mixture was stirred for 18 hours at ambient temperature. Extraction was carried out 3 times with methylene chloride, followed by washing with salt water and drying to obtain 2.88 g of the expected product (white crystals) melting at 51°–52° C.

| I.R.: | (CHCL$_3$) cm$^{-1}$ |
|---|---|
| NH$_2$ | 3398–3381–3321 |
| NH$_2$ def | 1617–1584 |
| C≡N | 2225 |

STAGE 2 pb 4-(4-imino-2-oxo-8-thia-1,3-diazaspiro[4.5]decan-3-yl)-2-(trifluoromethyl)-benzonitrile Using the procedure of Stage 2 of Example 1, 1.42 g of the product of Stage 1, 14 ml of 1,2-dichloroethane and 0.5 ml of triethylamine were reacted and the reaction medium was taken to a temperature between −10° C. and −5° C. over about 20 minutes. 9.1 ml of the product of the preparation of Example 7 of the European Patent Application EP 0,494,819 were added and the mixture was allowed to return to ambient temperature. The reaction medium stood for 80 minutes, followed by drying and purifying on silica with methylene chloride-acetone: 9–1 as eluant to obtain 2.49 g of the expected product (white crystals) melting at 226°–227° C.

| I.R.: | (nujol) cm$^{-1}$ |
|---|---|
| NH | 3330–3250–3210–3170–3120 |
| C≡N | 2240 |
| C=O | 1750 |
| C=N | 1675–1658 |
| Aromatics | 1612–1572–1510. |

EXAMPLE 13

4-(2,4-dioxo-8-thia-1,3-diazaspiro[4.5]-decan-3-yl)-2-(trifluoromethyl)-benzonitrile Using the procedure of Example 2, 2.34 g of the product of Example 12, 25 ml of methanol and 5 ml of chloroform were reacted and 4.5 ml of 2N hydrochloric acid were added. The reaction medium was refluxed for one hour and after purification on silica with methylene chloride-acetone: 95–5 as eluant, crystallization from isopropanol was carried out to obtain 368 mg of the expected product (white crystals) melting at 209°–210° C.

| I.R.: | (nujol) cm$^{-1}$ |
|---|---|
| OH/NH | 3340 |
| C≡N | 2245 |
| >C=O | 1781–1736 |
| Aromatics | 1612–1576–1508. |

EXAMPLE 14

4-(2,4-dioxo-1-(4-hydroxybutyl)-8-thia-1,3-diazaspiro[4.5]-decan-3-yl)-2-(trifluoromethyl)-benzonitrile Using the procedure of Example 3, 55 mg of 50% sodium hydride and 355 mg of the product of Example 13 were reacted and 2.5 ml of dimethylsulfoxide were added dropwise over 20 minutes. Rinsing was carried out with 0.5 ml of dimethylsulfoxide and 20 minutes after the release of hydrogen had stopped, 0.41 g of 4-iodo-butoxy-trimethylsilane were added. The reaction medium was poured into 25 ml of water containing 0.1 g of monopotassium phosphate and extraction was carried out 3 times with ether. The organic phase was washed with water, then with salt water and dried. The resultant product was taken up in 10 ml of methanol and 1 ml of 2N hydrochloric acid and left for 30 minutes. It was poured into 30 ml of 50% sodium chloride and extraction was carried out 3 times with ethyl acetate. The extracts were washed with salt water and dried. Purification was carried out on silica with methylene chloride-acetone: 9–1 as eluant to obtain 317 mg of the expected product (white crystals) melting at 139°–140° C.

| I.R.: | (CHCl$_3$) cm$^{-1}$ |
|---|---|
| OH | 3628 |
| C≡N | 2235 |
| >C=O | 1774–1722 |
| Aromatics | 1615–1601–1505. |

EXAMPLE 15

4-(2,4-dioxo-8,8-dioxido-8-thia-1,3-diazaspiro[4.5]-decan-3-yl)-2-(trifluoromethyl)-benzonitrile 355 mg of the product of Example 12 and 4 ml of methylene chloride were mixed together and 990 mg of m-chloroperbenzoic acid and 20 ml of methylene chloride were added over 20 minutes between 22° and 25° C. The solution was rinsed with 1 ml of methylene chloride and stood for one hour. 15 ml of sodium thiosulfate were added and vigorous stirring was carried out for 10 minutes. 15 ml of a saturated solution of sodium bicarbonate were added, followed by extracting 3 times with ethyl acetate, washing with water, then with salt water and drying. The residue was purified on silica with methylene chloride-acetone: (95–5) as eluant followed by crystallizing from isopropanol to obtain 365 mg of the expected product (white crystals) melting at 257°–258° C.

| I.R.: | (nujol) cm$^{-1}$ |
|---|---|
| C≡N | 2235 |
| >=O | 1790–1735 |
| SO$_2$ | 1297–1133 |
| Aromatics | 1613–1575–1508 |

EXAMPLE 16

4-(2,4-dioxo-8-oxido-8-thia-1,3-diazaspiro[4.5]-decan-3-yl)-2-(trifluoromethyl)-benzonitrile (isomer "A")

355 mg of the product of Example 13, 20 ml of methanol and 4 ml of aqueous solution of sodium m-periodate were mixed together and taken to reflux. The methanol was evaporated off and the residue was taken up in 20 ml of water. Extraction was carried out 4 times with ethyl acetate and the organic phase was washed with salt water and dried. Purification was carried out on silica with methylene chloride-methanol: 95-5 as eluant to obtain 900 mg of isomer "A" sulfoxide. It was crystallized from acetone to obtain 292 mg of the expected product called isomer "A" melting at 260°–277° C.

| I.R.: | (nujol) cm$^{-1}$ |
|---|---|
| General adsorption NH/OH | |
| C≡N | 2235 |
| >=O | 1789–1725 |
| S–>O | 1010 |
| Aromatics | 1612–1572–1509. |

EXAMPLE 17

4-(2,4-dioxo-8-oxido-8-thia-1,3-diazaspiro[4.5]-decan-3-yl)-2-(trifluoromethyl)-benzonitrile (isomer "B")

Using the procedure of Example 16 and purification carried out on silica with methylene chloride-methanol 9-1 as eluant, 80 mg of isomer "B" sulfoxide were obtained which was crystallized from acetone to obtain 72 mg of the expected product called isomer "B" melting at 295° C.

| I.R.: | (nujol) cm$^{-1}$ |
|---|---|
| Adsorption NH/OH | |
| C≡N | 2240 |
| >C=O | 1797–1730 |
| S–>O | 1015 |
| Aromatics | 1618–1580–1509. |

EXAMPLE 18

Ethyl 3-(4-cyano-3-(trifluoromethyl)-phenyl)-2,4-dioxo-8-thia-1,3-diazaspiro[4.5]-decan-1-butanoate Using the procedure of Example 6, 96 mg of 50% sodium hydride and 390 mg of the product of Example 13 were reacted and 2.5 ml of dimethylsulfoxide were introduced over about 20 minutes. The solution was rinsed with 0.5 ml of dimethylsulfoxide and 20 minutes after the release of hydrogen had stopped, 370 mg of ethyl 4-bromobutyrate were added. The solution was taken to 40° C. for one hour and was then poured into 15 ml of ice-cooled water containing 0.1 g on monopotassium phosphate. Extraction was carried out 4 times with ether and the organic phase was washed with water, then with salt water and dried. After purification on silica with methylene chloride-ethyl acetate: 95-5 as eluant, 449 mg of the expected product (friable white foam) were obtained.

| I.R: | (CHCl$_3$) cm$^{-1}$ |
|---|---|
| C≡N | 2236 |
| >=O | 1774–1723 |
| Aromatics | 1615–1575–1505. |

EXAMPLE 19

3-(4-cyano-3-(trifluoromethyl)-phenyl)-2,4-dioxo-8-thia-1,3-diazaspiro[4.5]decane-1-butanoic acid Using the procedure of Example 7, 440 mg of the product of Example 18, 20 ml of methanol and 2 ml of 2N sodium hydroxide were reacted and the mixture was stirred for 3 hours and 30 minutes at ambient temperature. 3 ml of 2N hydrochloric acid were added and purification was carried out on silica with methylene chloride-methanol: 95-5 as eluant to obtain 346 mg of the expected product (white crystals) melting at 197°–198° C.

| I.R.: | $(CHCl_3)$ cm$^{-1}$ |
|---|---|
| C≡N | 2235 |
| >=O | 1770–1725 |
| Acid | 1710 |
| Aromatics | 1615–1575–1505. |

EXAMPLE 20

4-(4-imino-8-methyl-2-thioxo-1,3,8-triazaspiro[4.5]-decan-3-yl)-2-(trifluoromethyl)-benzonitrile

STAGE 1

4-amino-1-methyl-piperidine-4-carbonitrile

Using the procedure of Stage 1 of Example 1, 8 ml of ammonium hydroxide, 1.58 g of ammonium chloride and 1.23 g of sodium cyanide were reacted and 2.5 ml of 1-methylpiperidone were added. The mixture was stirred for 18 hours at ambient temperature, followed by extraction r3 times with chloroform. The organic phase was washed with salt water and dried to obtain 2.41 g of the expected product (orange-yellow syrup).

| I.R.: | $(CHCl_3)$ cm$^{-1}$ |
|---|---|
| $NH_2$ | 3378–3320 |
| C≡N | 2226 |
| $NH_2$ def. | 1602 |

STAGE 2

4-(4-imino-8-methyl-2-thioxo-1,3,8-triazaspiro[4.5]-decan-3-yl)-2-(trifluoromethyl)-benzonitrile Using the procedure of Stage 2 of Example 1, 140 mg of the product of Stage 1, 1.5 mg of 1,2-dicholorethane and 0.1 ml of triethylamine were reacted and 230 mg of the product of Example 11 of European Patent Application EP 0,494,819 and 1.5 ml of 1,2- dichloroethane were added dropwise. The reaction medium stood for 2 hours and then was evaporated to dryness. The residue was purified on silica with methylene chloride-acetone: 8–2 as eluant to obtain 315 mg of the expected product (ivory crystals) melting at >264° C.

| I.R.: | (nujol) cm$^{-1}$ |
|---|---|
| NH | 3190 |
| C≡N | 2240 |
| >=NH | 1700–1688–1678 |
| Aromatics | 1618–1580–1518–1505. |

EXAMPLE 21

4-(8-methyl-4-oxo-2-thioxo-1,,3,8-triazaspiro[4.5]-decan-3-yl)-2-(trifluoromethyl)-benzonitrile 300 mg of the product of Example 20, 6 ml of methanol and 1.5 ml of 2N hydrochloric acid were mixed together and refluxed for one hour, then returned to ambient temperature. The reaction medium was poured into 20 ml of 50% ammonium hydroxide saturated with sodium chloride and extraction was carried out 3 times with ethyl acetate. The extracts were dried and purification was carried out on silica with methylene chloride-methanol: 9-1 as eluant to obtain 260 mg of the expected product (white crystals) melting at 229°–230° C.

| I.R.: | (nujol) cm$^{-1}$ |
|---|---|
| OH/NH | 3330–3340 + associated |
| C≡N | 2236 |
| C=O | 1757 |
| Aromatics | 1614–1580–1514–1502. |

EXAMPLE 22

4-(4-imino-8-methyl-2-oxo-1,3,8-triazaspiro[4.5]-decan-3-yl)-2-(trifluoromethyl)-benzonitrile Using the procedure of Stage 2 of Example 20, 153 mg of the product of Stage 1 of Example 20, 1.5 ml of 1,2-dichlorethane and 0.1 ml of triethylamine were reacted and the solution was placed in an ice-cooled water bath. 1 ml of the product of Example 7 of European Patent Application EP 0,494,819 was added and the mixture was allowed to return to ambient temperature. The reaction medium stood for one hour, was dried and the residue was purified on silica with methylene chloride-methanol: 7-3 as eluant to obtain 277 mg of the expected product (white crystals) melting at 199°–200° C.

| I.R.: | (nujol) cm$_{-1}$ |
|---|---|
| NH | 3290–3240–3130 |
| C≡N | 2224 |
| C=O | 1746 |
| C=NH | 1677–1669 |
| Aromatics | 1609–1568–1512. |

EXAMPLE 23

4-(2,4-dioxo-8-methyl-1,3,8-triazaspiro[4.5]-decan-3-yl)-2-(trifluoromethyl)-benzonitrile Using the procedure of Example 2, 3 g of the product of Example 22, 70 ml of methanol and 17 ml of 2N hydrochloric were reacted and the solution was refluxed for 90 minutes. It was poured into 200 ml of ammonium hydroxide +100 g of ice saturated with sodium chloride and extraction was carried out 4 times with ethyl acetate. The extracts were washed with salt water, dried and purified on silica with methylene chloride-methanol: 9-1 as eluant. After crystallization from methylene chloride-isopropyl ether, 2.12 g of the expected product (white crystals) melting at 188°–189° C were obtained.

| I.R.: | $(CHCl_3)$ cm$^{-1}$ |
|---|---|
| =C—NH | 3445 |
| C≡N | 2230 |
| >=O | 1789–1729 |
| Aromatics | 1615–1576–1505. |

EXAMPLE 24

4-(8,8-dimethyl)-2,4-dioxo-7,9-dioxa-1,3-diazaspiro-[4.5] decan-3-yl)-2-(trifluoromethyl)-benzonitrile

STAGE 1

1,3 bis-[(tetrahydro-2H-pyran-2-yl)oxy]-2-propanone 9 g of 2,5-dihydroxy-1,4-dioxane-2,5-dimethanol were introduced into 60 ml of dioxane and the suspension was taken to about 70° C. for 15 minutes, then taken to ambient temperature.

Then, 20 ml of 3,4-dihydro-2H-pyran and 300 mg of monohydrated p-toluene sulfonic acid were added. The temperature was held at about 40° C. and then the reaction medium stood overnight at ambient temperature. It was then poured into a mixture of 300 ml of a saturated solution of sodium bicarbonate +10 ml of triethylamine and extraction was carried out 4 times with methylene chloride. The organic phase was washed with salt water and dried. After purification by passing through silica with ethyl cycloacetate/triethylamine: 8/2 as eluant, 17 g of the expected product (pale yellow syrup) were obtained.

| I.R.: | $(CHCl_3)$ $cm^{-1}$ |
|---|---|
| Absence OH | |
| C=O | 1736 |

STAGE 2

2-amino-3-[(tetrahydro-2H-pyran-2-yl)-oxy]-2-[((tetrahydro-2H-pyran-2-yl)-oxy)-methyl]-propanenitrile 5.6 g of the product of Stage 1 were introduced into 8 ml of ammonium hydroxide and the mixture was brought to about −5° C. 1.58 g of ammonium chloride and 1.23 g of sodium cyanide were added successively and the mixture was allowed to return to ambient temperature for about 40 minutes, then heated to 40° C.±5° C. with stirring overnight. The reaction medium was returned to ambient temperature and extraction was carried out 3 times with chloroform. The organic phase was washed with salt water and dried. After purification on silica with ethyl cycloacetate/triethylamine: 3/7 as eluant, 4.41 g of the expected product (pale yellow syrup) were obtained.

| IR | $CHCl_3(cm^{-1})$ |
|---|---|
| —CN | 2235 |
| $NH_2$ | 3390–3317 |

STAGE 3

4-(5-imino-2-oxo-4,4-bis[((tetrahydro-2H-pyran-2-yl)-oxy)-methyl)]-1-imidazolidinyl]-2-(trifluoromethyl)-benzonitrile 570 mg of the product of Stage 2 were introduced into 5 ml of isopropyl ether and 0.28 ml of triethylamine and the mixture was brought to −30° C. Then, a solution of 1,2-dichloroethane at 18.4 g % g and 2.32 g of the product of preparation 1 were added over one hour. 4 ml of methylene chloride were added and then the reaction medium was allowed to return to ambient temperature. It stood for about 2 hours and was dried. After purification on silica with methylene chloride/acetone 9/1 as eluant, 700 mg of the expected product were obtained.

| IR | $CHCl_3$ $(cm^{-1})$ |
|---|---|
| NH | 3442–3317 |
| —CN | 2235 |
| C=O | 1757 |
| C=N | 1670 |
| Aromatics | 1614–1575–1505. |

STAGE 4

4-(4,4-bis(hydroxymethyl)-2,5-dioxo-1-imidazolidinyl)-2-(trifluoromethyl)-benzonitrile 300 mg of the product of Stage 3 were introduced into 3 ml of methanol and 1.5 ml of 2 N hydrochloric acid and the mixture was refluxed for 90 minutes. It was returned to ambient temperature and poured into 5 ml of sodium bicarbonate. Extraction was carried out 4 times with ethyl acetate and the extracts were washed with a saturated solution of sodium chloride and dried. Purification was carried out on silica with methylene chloride-methanol: 9/1 as eluant. The resultant product was taken up in 20 ml of isopropanol at reflux and then concentrated to obtain 225 mg of the expected product (white crystals) melting at 207°–208° C.

| IR | NUJOL $(cm^{-1})$ |
|---|---|
| OH/NH | 3525–3365–3250 |
| CN | 2240 |
| C=O | 1778–1738 |
| Aromatics | 1618–1578–1506. |

STAGE 5

4-(8,8-dimethyl)-2,4-dioxo-7,9-dioxa-1,3-diazaspiro[4.5]decan-3-yl)-2-(trifluoromethyl)-benzonitrile 0.329 g of the product of Stage 4, 0.5 ml of 2,2-dimethoxypropane, 0.02 g of p-toluene sulfonic acid and 5 ml of acetone were mixed together and stirred for 4 hours. Then, the mixture was hydrolyzed with a solution of sodium bicarbonate and extraction was carried out with ethyl acetate. The organic phases were collected, washed with water, dried, filtered and concentrated. Chromatography on silica was carried out with methylene chloride-acetone: 95–5 as eluant. After crystallization from isopropanol, 0.240 g of the expected product (white crystals) melting at 203° C. were obtained.

| IR: | NUJOL $(cm^{-1})$ |
|---|---|
| CN | 2240 |
| C=O | 1782–1730 |
| Aromatics | 1615–1580–1507. |

EXAMPLE 25

Tablets were prepared containing 100 mg of the product of Example 3 and sufficient excipient of lactose, starch, talc, magnesium stearate for a tablet of 300 mg.

PHARMACOLOGICAL STUDY

Study of the affinity of the products for the androgen receptor

Male Sprague Dawley EOPS rats weighing 180–200 g, castrated 24 hours previously, were sacrificed and the prostates were removed, weighed and homogenized at 0° C. using a Potter glass, in a buffered solution (10 mM Tris, 0.25M saccharose, 0.1 mM PMSF (phenylmethanesulfonylfluoride), 20 mMsodium molybdate, HCl pH 7.4; 2 mM of DTT (DL dithiothreitol) were added extemporaneously thereto at a rate of 1 g of tissue per 8 ml of buffer. The homogenate was then ultracentrifuged at 0° C. for 30 minutes at 209,000 g. Aliquots of the supernatant obtained (=cytosol) were incubated for 30 minutes and for 24 hours at 0° C. with a constant concentration (T) of tritiated testosterone and in the presence of increasing concentrations (0 to $2500.10^{-9}M$), either of unlabelled testosterone, or of the products to be tested. The concentration of bound tritiated testosterone (B) was then measured in each incubate by the method of adsorption on carbon dextran.

Calculation of the relative bond affinity (RBA).

The following 2 curves were drawn: the percentage of bound tritiated hormone B/T as a function of the logarithm of the concentration of the unlabelled reference hormone and B/T as a function of the logarithm of the concentration of the unlabelled tested product. The straight line of the equation $I_{50}=(B/Tmax+B/Tmin)/2$ was determined.

B/T max=% of the bound tritiated hormone for an incubation of this tritiated hormone at the concentration (T).

B/T min=% of the bound tritiated hormone for an incubation of this tritiated hormone at the concentration (T) in the presence of a large excess of unlabelled hormone $(2500.10^{-9}M)$.

The intersections of the straight line $I_{50}$ and the curves allowed the evaluation of the concentrations of the unlabelled reference hormone (CH) and of the tested unlabelled product (CX) which inhibit by 50% the binding of the tritiated hormone on the receptor. The relative bond affinity (RBA) of the tested product was determined by the equation RBA=100 (CH)/(CX). The following results were obtained, expressed in RBA.

| Reference product (Testosterone):100 | |
|---|---|
| Product of Examples | RBA: Incubation 24 hours |
| 3 | 6 |
| 10 | 5 |

Various modifications of the products and method of the invention may be made without departing from the spirit or scope thereof and it is to be understood that the invention is intended to be limited only as defined in the appended claims.

What we claim is:

1. A method of inducing antiandrogenic activity in warm-blooded animals comprising administering to said warm-blooded animals an antiandrogenically effective amount of a compound of the formula

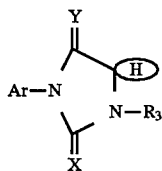

wherein (H) is a-saturated heterocyclic with 4 to 7 ring members containing: either an oxygen, nitrogen or optionally oxidized sulfur, the nitrogen being optionally substituted by $R_3$ or the saturated heterocyclic contains two oxygen and optionally one boron which is atom substituted by phenyl, the heterocycle being optionally substituted on a carbon atom with oxo, at least one alkyl optionally substituted, or cycloalkyl of 4 to 7 members, Ar is aryl optionally substituted by at least one member of the group consisting of i) halogen, cyano, nitro, trifluoromethyl, trifluoromethoxy, hydroxyl, free, salified, esterified or amidified carboxy,

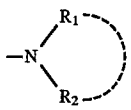

in which the nitrogen atom is optionally oxidized and $R_1$ and $R_2$ are individually selected from the group consisting of hydrogen and optionally substituted alkyl or form together with the nitrogen atom to which they are attached a monocyclic of 5, 6 or 7 ring members or a condensed ring of 8 to 14 ring members, both optionally containing, at least one heteroatom selected from the group consisting of oxygen, nitrogen and sulfur, and being optionally substituted, iii) optionally substituted alkyl, alkoxy, alkylthio and arylthio,

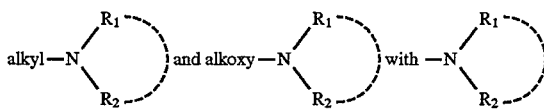

as defined above,

X is oxygen or sulfur,

Y is oxygen or sulfur or NH, $R_3$ is selected from the group consisting of hydrogen, aryl and alkyl, alkenyl and alkynyl of up to 6 carbon atoms optionally interrupted by at least one oxygen, nitrogen or optionally oxidized sulfur, all being optionally substituted, the substituents of the ring

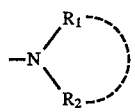

and the alkyl, aryl, alkoxy, alkenyl and alkynyl indicated above as optionally substituted are selected from the group consisting of halogen, optionally salified, esterified or etherified hydroxy, alkoxy, aryloxy, alkyl, haloalkoxy, haloalkyl, mercapto, alkylthio and arylthio in which the sulfur is optionally oxidized, acyl and acyloxy of an organic carboxylic acid of up to 6 carbon atoms, free, salified, esterified or amidified carboxy, cyano, nitro, amino, mono or dialkylamino, aryl and arylalkyl, the last two being optionally substituted by at least one member of the group consisting of halogen, hydroxyl, alkyl and alkoxy of up to 6 carbon atoms, trifluoromethyl trifluoromethoxy, nitro, cyano, free, salified or esterified carboxy and tetrazolyl, all the sulfurs being optionally oxidized into sulfoxide or sulfone, with the proviso Ar is not unsubstituted phenyl, x and y are not both oxygen, H is not piperidino substituted with isopropyl, n-butyl or benzyl and $R_3$ is not hydrogen, acyl or phenyl, the said products of formula I being in all the possible racemic, enantiomeric and diastereoisomeric isomer forms and their non-toxic, pharmaceutically addition salts with acids or bases.

2. The method of claim 1 where in Ar is an optionally substituted phenyl or pyridyl.

3. The method of claim 1 where a compound of formula I is selected from the group consisting of 4-(2,4-dioxo-1-(4-hydroxybutyl)-8-oxa-1,3-diazaspiro (4.5)decan-3-yl)-2-(trifluoromethyl)-benzonitrile, 4-(2,4-dioxo-1-(2-fluoroethyl)-8-oxa-1,3-diazaspiro (4.5)decan-3-yl)-2-(trifluoromethyl)-benzonitrile, 3-(4-cyano-3-(trifluoromethyl)-phenyl)-2,4-dioxo-8-oxa-1,3-diazaspiro (4.5)decane-1-acetonitrile and 4-(2,4-dioxo-1-(4-hydroxybutyl)-8-thia-1,3-diazaspiro (4.5)decan-3-yl)-2-(trifluoromethyl)-benzonitrile.

* * * * *